(12) United States Patent
Suga (10) Patent No.: US 10,105,034 B2
(45) Date of Patent: Oct. 23, 2018

(54) ENDOSCOPE APPARATUS

(71) Applicant: OLYMPUS CORPORATION, Hachioji-shi, Tokyo (JP)

(72) Inventor: Takeshi Suga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/607,483

(22) Filed: May 27, 2017

(65) Prior Publication Data

US 2017/0258297 A1 Sep. 14, 2017

Related U.S. Application Data

(63) Continuation of application No. PCT/JP2015/083872, filed on Dec. 2, 2015.

(30) Foreign Application Priority Data

Mar. 30, 2015 (JP) .................................. 2015-069627

(51) Int. Cl.
*A61B 1/05* (2006.01)
*G02B 23/24* (2006.01)
(Continued)

(52) U.S. Cl.
CPC ...... *A61B 1/00009* (2013.01); *A61B 1/00096* (2013.01); *A61B 1/00193* (2013.01);
(Continued)

(58) Field of Classification Search
CPC ......... A61B 1/00009; A61B 1/04; A61B 1/05; G02B 23/24; G02B 23/2415; G03B 35/00
See application file for complete search history.

(56) References Cited

U.S. PATENT DOCUMENTS 5,860,912 A * 1/1999 Chiba ................ A61B 1/00059
348/45
6,720,988 B1 * 4/2004 Gere .................. A61B 1/00183
348/45
(Continued)

FOREIGN PATENT DOCUMENTS

JP 08056891 A 3/1996
JP 2004309930 A 11/2004
(Continued)

OTHER PUBLICATIONS

Parchami et al. ("Endoscopic stereo reconstruction: A comparative study," International Conference on Engineering in Medicine and Biology Society, Aug. 26-30, 2014).*
(Continued)

*Primary Examiner* — Yubin Hung
(74) *Attorney, Agent, or Firm* — Holtz, Holtz & Volek PC (57) ABSTRACT

There is provided an endoscope apparatus which enables to observe a three-dimensional image which is easy to view even in close observation.
An endoscope apparatus, comprises:
  optical systems which form images for a left-eye and a right-eye respectively;
  an image pickup element which captures the two images and generates pictorial images for the left eye and the right eye; and
  at least one image processing unit which carries out processing of a pictorial image signal from the image pickup element and creates a stereoscopic image that can be displayed on a monitor, wherein
  the endoscope apparatus satisfies the following conditional expression (1)

$0.3 < CP \times (1 + Dt1) < 7$, and $CP \leq 10$     (1)

(Continued)

where,
CP denotes a distance (mm) from a surface nearest to object of the optical system up to an object, when an amount of left and right shift of the left-eye pictorial image and the right-eye pictorial image becomes 0, at a center of a monitor screen, and
Dt1 denotes a distortion in length at the maximum image height.

3 Claims, 12 Drawing Sheets (51) Int. Cl.
| | |
|---|---|
| *A61B 1/00* | (2006.01) |
| *A61B 1/04* | (2006.01) |
| *G03B 35/08* | (2006.01) |
| *G03B 35/00* | (2006.01) |
| *G03B 15/14* | (2006.01) |
| *G02B 13/04* | (2006.01) |

(52) U.S. Cl.
CPC .............. *A61B 1/04* (2013.01); *A61B 1/05* (2013.01); *G02B 23/24* (2013.01); *G02B 23/243* (2013.01); *G03B 15/14* (2013.01); *G03B 35/00* (2013.01); *G03B 35/08* (2013.01); *G02B 13/04* (2013.01); *G02B 23/2415* (2013.01)

(56) References Cited

U.S. PATENT DOCUMENTS

| | | | | |
|---|---|---|---|---|
| 8,167,793 B2* | 5/2012 | Scott | ............... | A61B 1/00009 |
| | | | | 600/160 |
| 8,608,645 B2* | 12/2013 | Boebel | ............... | A61B 1/00193 |
| | | | | 600/111 |
| 8,672,838 B2* | 3/2014 | McDowall | ......... | A61B 1/00009 |
| | | | | 600/129 |
| 2004/0263613 A1 | 12/2004 | Morita | | |
| 2009/0292168 A1* | 11/2009 | Farr | ..................... | A61B 1/0607 |
| | | | | 600/109 |
| 2012/0300032 A1 | 11/2012 | Ookoba | | |
| 2013/0300829 A1* | 11/2013 | Urasaki | .............. | A61B 1/00009 |
| | | | | 348/45 |
| 2014/0177043 A1 | 6/2014 | Togino et al. | | |
| 2015/0168710 A1* | 6/2015 | Zobel | ................. | A61B 1/00105 |
| | | | | 348/45 |

FOREIGN PATENT DOCUMENTS

| | | |
|---|---|---|
| JP | 2007068876 A | 3/2007 |
| JP | 2012245056 A | 12/2012 |
| WO | 2013108500 A1 | 7/2013 |

OTHER PUBLICATIONS

Dhiraj et al. ("Development of 3D endoscope for minimum invasive surgical system," International Conference on Signal Propagation and Computer Technology, Jul. 12-13, 2014).*

Lu et al. ("Stereoscopic imaging technology for medical video endoscope," Proceedings of SPIE, vol. 4916, Sep. 12, 2002).*

International Search Report (ISR) and Written Opinion dated Feb. 23, 2016 issued in International Application No. PCT/JP2015/083872.

International Preliminary Report on Patentability (IPRP) dated Oct. 12, 2017 issued in counterpart International Application No. PCT/JP2015/083872.

* cited by examiner

ENDOSCOPE APPARATUS

CROSS-REFERENCE TO RELATED APPLICATION

The present application is a continuation application of PCT/JP2015/083872 filed on Dec. 2, 2015 which is based upon and claims the benefit of priority from Japanese Patent Application No. 2015-069627 filed on Mar. 30, 2015; the entire contents of which are incorporated herein by reference.

BACKGROUND OF THE INVENTION

Field of the Invention

The present invention relates to an endoscope apparatus, and particularly to an endoscope apparatus which captures an image that can be displayed stereoscopically.

Description of the Related Art

An endoscope is an apparatus that has been used widely in a medical field and an industrial field. In the medical field, pictorial images of various sites in an abdominal cavity are achieved by an endoscope inserted into the abdominal cavity. A diagnosis of a site observed is carried out by using these pictorial images. Thus, endoscopes are used for observation and diagnosis of various sites in the abdominal cavity.

In the observation by an endoscope, a plurality of images having a parallax are captured, and accordingly, by fusing the plurality of pictorial images, a pictorial image is displayed stereoscopically (3D display). Such endoscopes which carry out a three-dimensional observation have been proposed in International Publication No. 2013-108500 and Japanese Patent Application Laid-open Publication No. 2012-245056.

SUMMARY OF THE INVENTION

According to an aspect of the present invention, an endoscope apparatus includes:

optical systems which form images for a left-eye and a right-eye respectively;

at least one image pickup element which captures the two images and generates pictorial images for the left eye and the right eye; and an image processing unit which carries out processing of a pictorial image signal from the image pickup element and creates a stereoscopic image that can be displayed on a monitor, wherein the endoscope apparatus satisfies the following conditional expression (1)

$$0.3 < CP \times (1+Dt1) < 7, \text{ and } CP \leq 10 \quad (1)$$

where,

CP denotes a distance (mm) from a surface nearest to object of the optical system up to an object, when an amount of left and right shift of the left-eye pictorial image and the right-eye pictorial image becomes 0, at a center of a monitor screen, and Dt1 denotes a distortion in length at the maximum image height.

DETAILED DESCRIPTION OF THE INVENTION

Reasons for and effects of having such arrangement for an endoscope apparatus according to the present embodiment will be described below by using accompanying diagrams. However, the present invention is not limited to embodiments described below.

Figure 1:
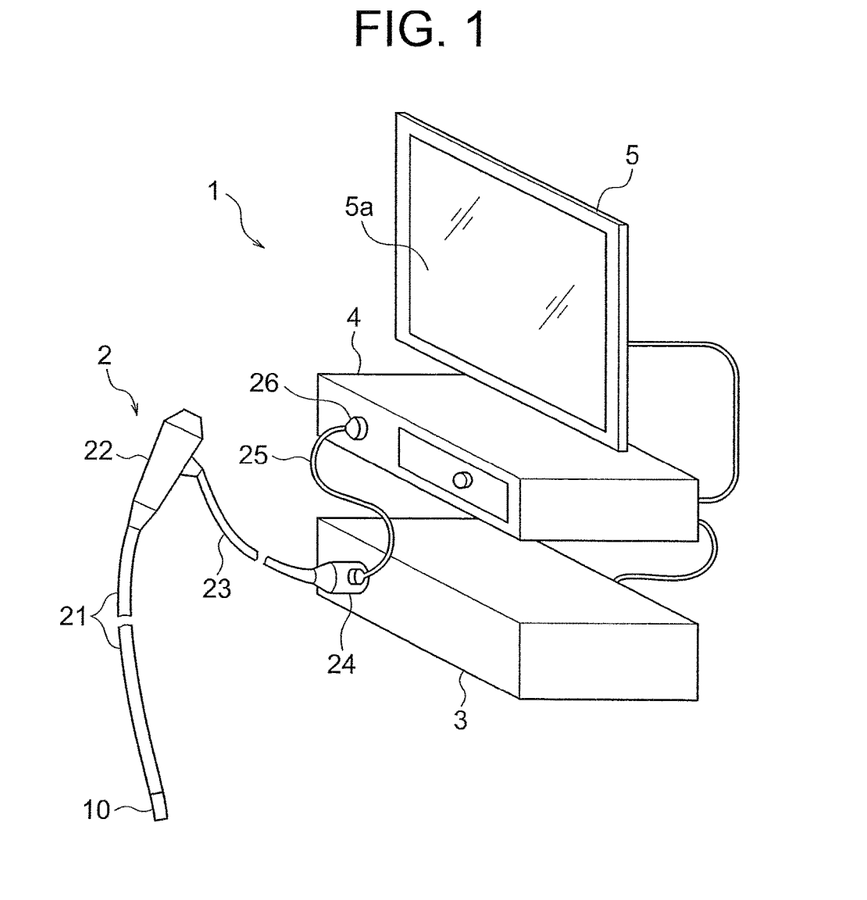
FIG. 1 is a diagram showing a schematic arrangement of an endoscope apparatus according to an embodiment of the present invention.

FIG. 1 is a diagram showing a schematic arrangement of an endoscope apparatus 1 according to the present embodiment.

As shown in FIG. 1, the endoscope apparatus 1 includes an electronic endoscope 2 in which an image pickup element 12 is built-in as an image pickup element (refer to FIG. 2A), a light source unit 3 having a light source which supplies illuminating light to the electronic endoscope 2, an image processing unit 4 which carries out signal processing with respect to the image pickup element 12 of the electronic endoscope 2, and a monitor 5 which displays an endoscope pictorial image by a video signal output through the image processing unit 4.

The electronic endoscope 2 includes an inserting portion 21 which is long, thin, and flexible, an operating portion 22 having a thick width which is formed at a rear end of the inserting portion 21, a front-end rigid portion 10, and a universal cord 23 which is extended from a side portion of the operating portion 22. An end portion of the universal cord 23 is provided with a connector portion 24 which is detachably connected to the light source unit 3. An end portion of a connecting cord 25 extended toward the connector portion 24 is provided with an electric connector portion 26 which is detachably connected to the image processing unit 4.

(First Embodiment)

Figure 2A:
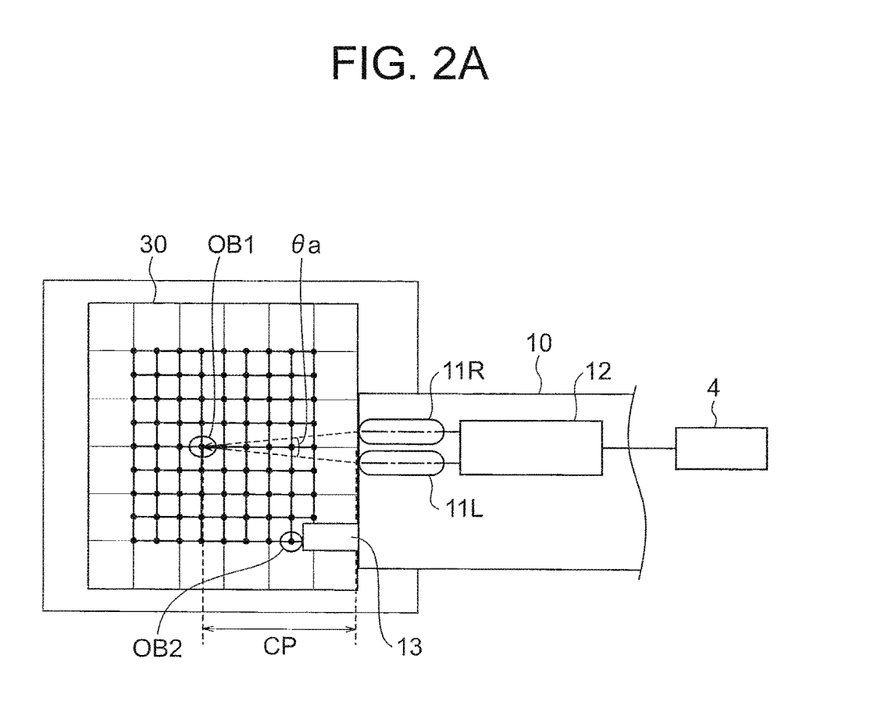
FIG. 2A is a diagram illustrating an object space of an endoscope apparatus according to a first embodiment.

FIG. 2A is a diagram showing a vicinity of the front-end rigid portion 10 of an endoscope apparatus according to a first embodiment of the present invention. The endoscope apparatus of the present embodiment has two optical systems namely, a right-eye optical system 11R and a left-eye optical system 11L. Details of the two optical systems will be described later.

In an object space 30, by the right-eye optical system 11R and the left-eye optical system 11L, a right-eye image and a left-eye image of an object OB is formed on an image pickup surface of the image pickup element 12. The image processing unit 4 carries out image processing to be described later on an output signal from the image pickup element 12. Moreover, the image processing unit 4 outputs a signal of a pictorial image for right eye and a pictorial image for left eye subjected to image processing to the monitor 5.

In FIG. 2A, an angle θa made by a straight line connecting a point at which an optical axis of the right-eye optical system 11R intersects a lens surface nearest to object, and the object OB, and a straight line connecting a point at which an optical axis of the left-eye optical system 11L intersects the lens surface nearest to object, and the object OB, is let to be an inward angle.

Figure 2B:
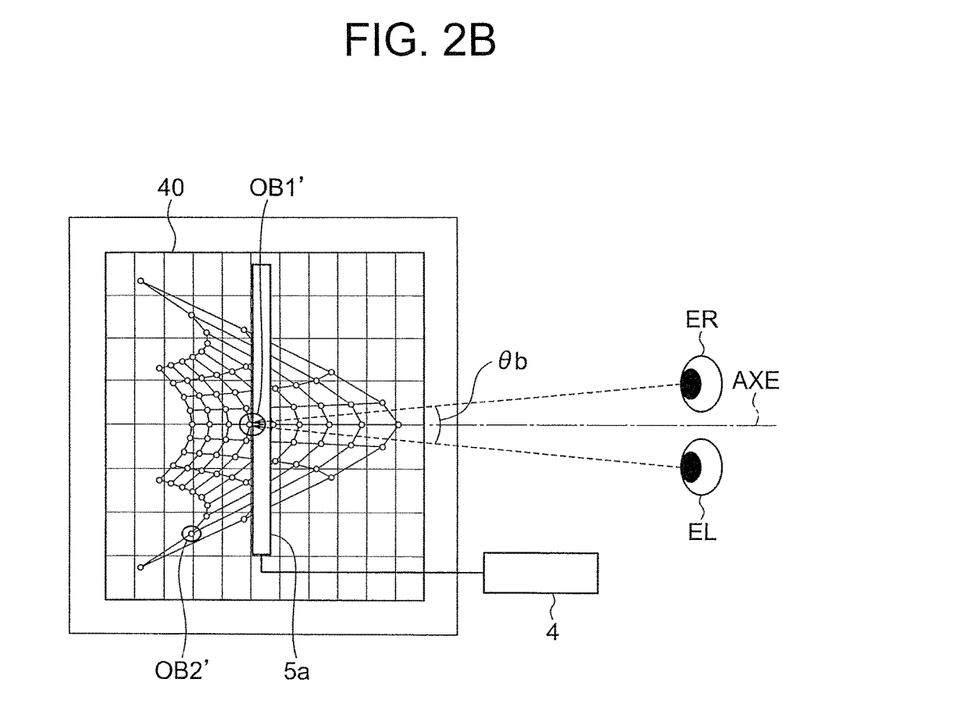
FIG. 2B is a diagram illustrating a reproducing space of the endoscope apparatus according to the first embodiment.

FIG. 2B is a diagram illustrating a reproducing of an object image OB' in the first embodiment. In a reproducing space 40, on the basis of a signal from the image processing apparatus 4, the pictorial image for right eye and the pictorial image for left eye are displayed on a monitor screen 5a of the monitor 5.

FIG. 2B shows a case in which the object image OB' is displayed on the monitor screen 5a of the monitor 5. An angle θb made by a straight line connecting a line of sight of a right eye ER of an observer and the object image OB' and a straight line connecting a line of sight of a left eye EL and the object image OB' is let to be an angle of convergence.

The present embodiment is the endoscope apparatus 1 having the optical systems 11R and 11L which form pictorial images for the left eye and the right eye respectively, the image pickup element 12 which acquires, or captures a parallax pictorial image for the left eye and the right eye, and the image processing unit 4 which carries out processing of a signal of the parallax pictorial image and creates a stereoscopic pictorial image that can be displayed on the monitor.

Moreover, it is desirable to satisfy the following conditional expression (1).

$$0.3 < CP \times (1+Dt1) < 7, \text{ and } CP \leq 10 \tag{1}$$

where,

CP denotes a distance (mm) from a surface nearest to object of the optical system up to an object, when an amount of left and right shift of the parallax pictorial image for the left eye and the right eye is 0, at a center of monitor screen, and Dt1 denotes a distortion in length at the maximum image height.

Figure 2C:
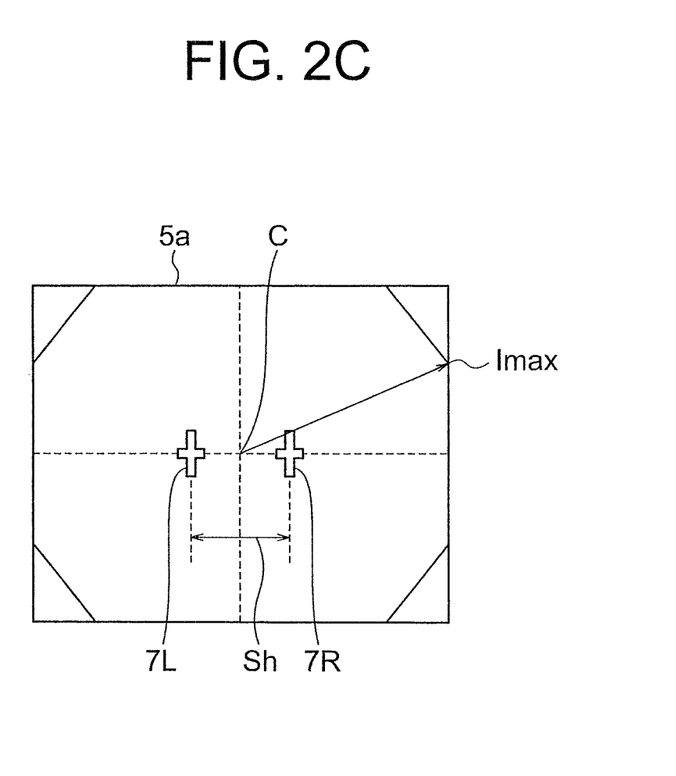
FIG. 2C is a diagram showing an amount of shift on a monitor screen.

A reason why an object image is viewed optically will be explained. FIG. 2C shows how the monitor screen 5a looks when viewed from the front side. A right-eye pictorial image 7R and a left-eye pictorial image 7L are displayed to be spaced apart by an amount of shift Sh. Moreover, the maximum image height Imax is indicated by a length from a center C of the monitor screen 5a up to the farthest position in an effective display area.

In a case in which the amount of shift Sh is zero, the right-eye pictorial image 7R and the left-eye pictorial image 7L coincide. Accordingly, the observer visually perceives that the object image OB' exists on the monitor screen 5a. Whereas, as shown in FIG. 2C, in a case in which the right-eye pictorial image 7R and the left-eye pictorial image 7L are spaced apart by the amount of shift Sh, the observer visually perceives that the object image OB' exists deep inside the monitor screen 5a.

In this manner, by changing the amount of shift Sh of the right-eye pictorial image 7R and the left-eye pictorial image 7L displayed on the monitor 5a, it is possible to set a position at which the object image OB' exists to be on the monitor 5a, at a far side space of the monitor screen 5a, and at a near side space of the monitor screen 5a. Accordingly, the observer can observe the object image OB' three-dimensionally. A control of the amount of shift Sh is carried out by the image processing unit 4.

Figure 7:
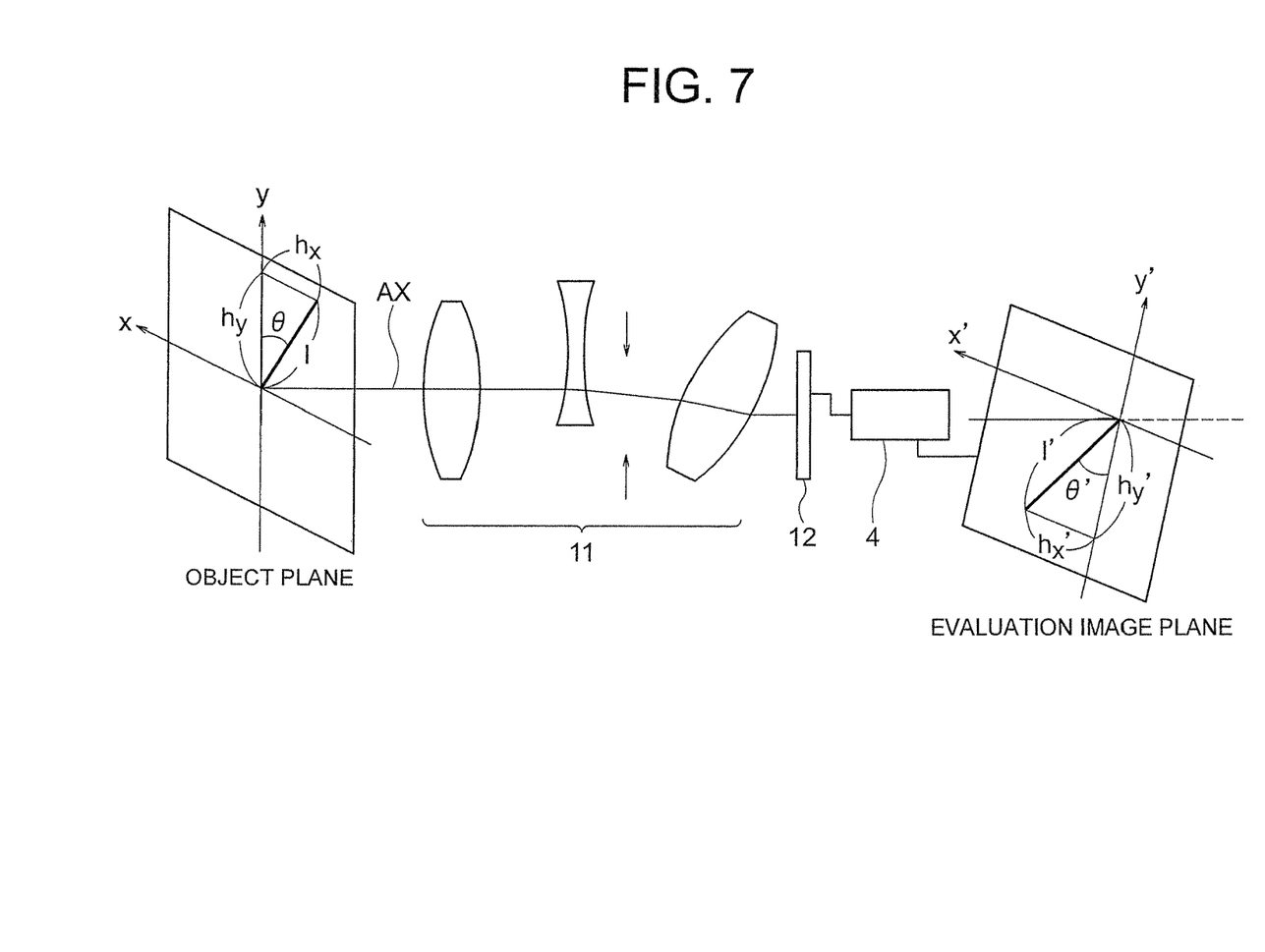
FIG. 7 is a diagram illustrating the distortion.

Furthermore, a relationship of as to how the object image OB' is viewed and a distortion in the present embodiment will be described below. FIG. 7 is a diagram illustrating the distortion in the present embodiment.

The distortion is defined by the following expression (A).

$$(|I'|-|\beta \times I|)/|\beta \times I| \tag{A}$$

where,

I denotes an object height at an object surface,

I' denotes an image height on the monitor screen, and

β denotes a lateral magnification.

In FIG. 7, for simplicity, the right-eye optical system 11R and the left-eye optical system 11L are let to be one, and is indicated by an optical system 11. An image of an object of height I is formed on the image pickup surface of the image pickup element 12. Moreover, a pictorial image signal from the image pickup element 12 is subjected to a predetermined processing by the image processing unit 4. Thereafter, an object image is formed on the monitor screen 5a of the monitor 5. The distortion is a distortion in a system including the optical system 11 and the image processing unit 4. In other words, it is a distortion in an image displayed on the monitor screen 5a which is a final evaluation image plane when an object plane is let to be a basis.

As mentioned above, by changing the amount of shift Sh of the right-eye pictorial image 7R and the left-eye pictorial image 7L on the monitor screen 5a, it is possible to set the position of the object image OB' in a depth direction viewed from the observer.

Furthermore, as to how it is possible to perceive visually the further enhanced three-dimensional effect of the object image OB' by distortion, will be described below.

Figure 3A:
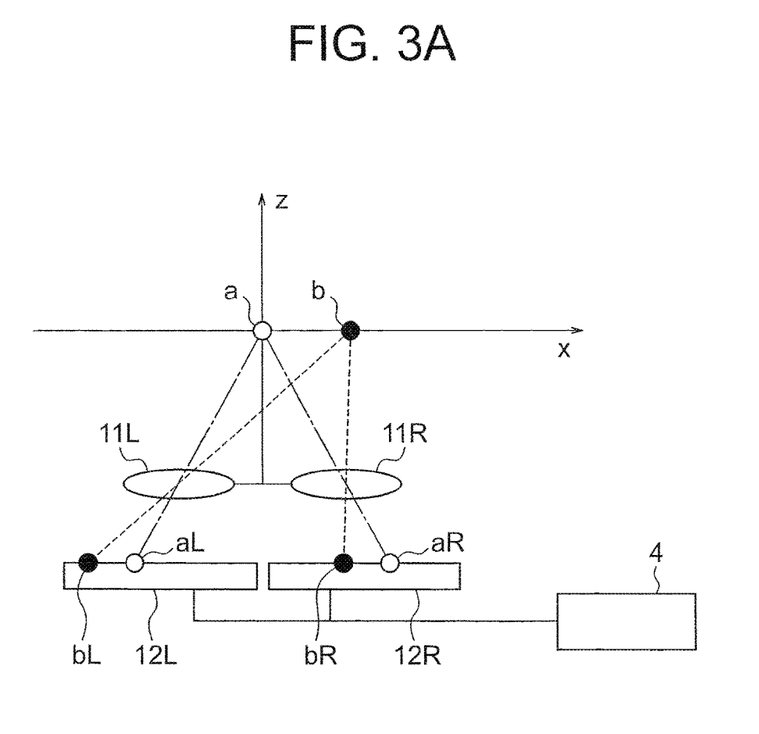
FIG. 3A is a diagram showing an object space for describing a distortion.

As shown in FIG. 3A, an image of an object a is formed as an image aR on an image pickup surface of a right-eye image pickup element 12R by the right-eye optical system 11R. Moreover, an image of the object a is formed as an image aL on an image pickup surface of a left-eye image pickup element 12L by the left-eye optical system 11L. In addition, an image of an object b is formed as an image bR on the image pickup surface of the right-eye image pickup element 12R by the right-eye optical system 11 R. Moreover, an image of the object b is formed as an image bL on the image pickup surface of the left-eye image pickup element 12L by the left-eye optical system 11L.

Figure 3B:
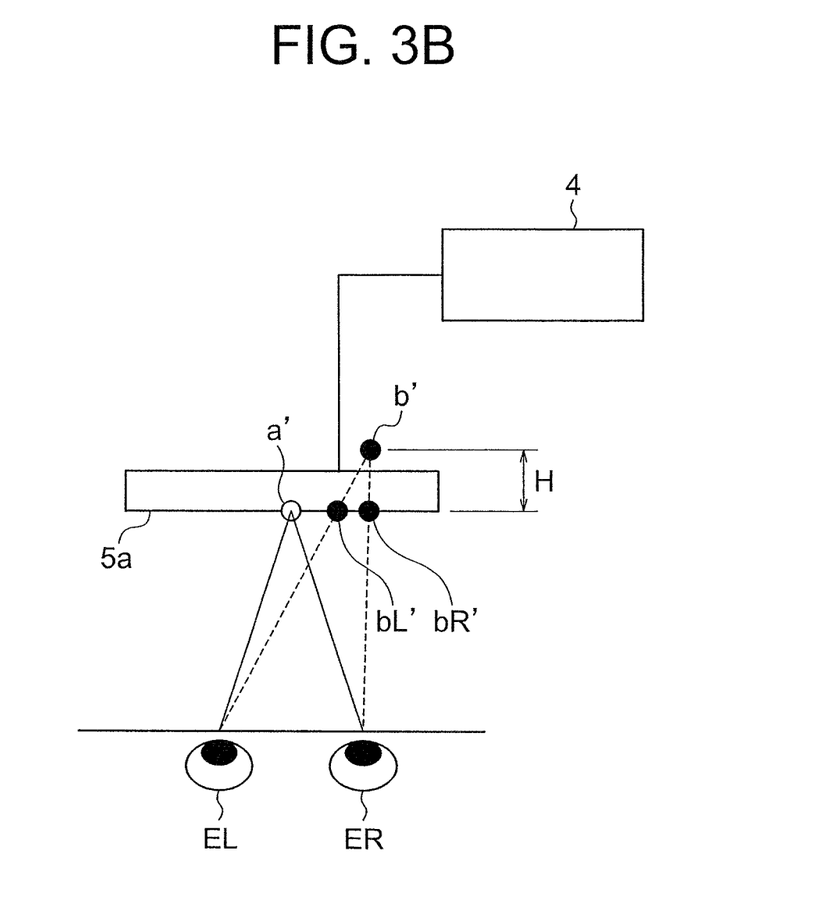
FIG. 3B is a diagram showing a reproducing space for describing the distortion.

Signals from the right-eye image pickup element 12R and the left-eye image pickup element 12L are output to the image processing unit 4. Moreover, as shown in FIG. 3B, on the basis of the signals from the image processing unit 4, an image a' of an object a is displayed on the monitor screen 5a. The observer visually perceives the image a' to have been positioned on the monitor screen 5a.

Moreover, on the basis of the signals from the image processing unit 4, two images bR' and bL' of the object b are displayed on the monitor screen 5a. The observer visually perceives the image b' upon fusion of two images bR' and bL', to have been positioned at a depth of distance H from the monitor screen 5a.

Here, when there is a distortion in a system from the optical system 11 up to the monitor screen 5a, respective positions of the two images bR' and bL' on the monitor screen 5a are further shifted. The distortion becomes large in a peripheral area than in a central area of the monitor screen 5a. Therefore, in a peripheral area of the monitor screen 5a where the image height is large, the image b' is visually perceived to have been positioned at further far side than the monitor screen 5a.

When a negative distortion or a so-called barrel distortion exists in the endoscope apparatus including an optical system and an image processing unit, with respect to a center of a screen of the monitor 5, in a periphery of the screen, a reproducing space exists in the depth direction for the observer. In other words, due to a negative barrel distortion, even when a flat surface is observed, on a monitor screen, it is reproduced as an object image having a bowl shape with a convex surface directed toward the observer.

The description will be continued returning to FIG. 2B. An object image OB1' is reproduced on the monitor screen 5a. Moreover, due to the negative distortion, an object image OB2' displayed on a periphery of the monitor screen 5a is reproduced in the depth direction of the monitor screen 5a. Consequently, since it is possible to make small the angle of convergence θb when observing the object image OB2', the observer is able to fuse images without any fatigue caused.

As mentioned above, in the present embodiment, it is desirable to satisfy conditional expression (1).

$$0.3 < CP \times (1+Dt1) < 7, \text{ and } CP \leq 10 \quad (1)$$

In the present embodiment, by a value falling below an upper limit value of CP×(1+Dt1), it is possible to reproduce an overall in-depth area of the object space, or in other words, an object image in the depth direction of the object image OB1' in FIG. 2B at a farther side than the monitor screen 5a. Furthermore, it is possible to reproduce also the object image OB2' viewed in a screen peripheral area of the monitor screen 5a at the depth direction of the monitor screen 5a. Consequently, the observer is able to fuse images in the overall area of the monitor screen 5a without any fatigue caused. For instance, a treatment tool 13 (see FIG. 2A) inserted into an endoscope is observed as an object in proximity of the peripheral portion of the monitor screen 5a. In the present embodiment, even when the line of sight is adjusted to the treatment tool 13 in the monitor screen, it is possible to fuse images without fatigue caused.

Moreover, by exceeding a lower limit value of CP×(1+Dt1), it is possible to limit the depth of the reproducing space. Consequently, it is possible to fuse object images in the overall area of the depth of field, such as the reproducing space range of 7 mm to 100 mm.

In the present embodiment, for reducing fatigue in the close observation, a near-depth boundary is reproduced on the monitor screen 5a, and the overall in-depth area is reproduced at the farther side than the monitor screen 5a. The near-depth boundary in a single-focus optical system is in a range of 3 mm to 8 mm. Consequently, it is desirable to set the CP value also in a range of 3 mm to 8 mm.

Moreover, in order to reduce fatigue due to vision of the treatment tool, it is desirable to reproduce an object positioned in the largest observation field at a distance of 3 mm from a lens surface nearest to object of the optical system, at an farther side than the monitor screen 5a.

In such manner, in a conventional technology, when the object is close, the object image is reproduced at a nearer side than the monitor screen 5a. In other words, at the near depth boundary, the angle of convergence becomes large. Consequently, the fatigue of the eyes of observer becomes substantial.

At the same time, in the present embodiment, the inward angle θa and the angle of convergence θb are different.

Particularly, it is desirable that the inward angle θa>the angle of convergence θb. Therefore, in the present embodiment, a degree of freedom of the inward angle θa is high. The angle of convergence θb in the present embodiment is a value determined by a distance between the observer and the monitor screen 5a, and a width of eyes of the observer.

It is preferable to satisfy the following conditional expression (1') instead of conditional expression (1).

$$0.4 < CP \times (1+Dt1) < 5.6, \text{ and } CP \leq 8 \quad (1')$$

Next, a numerical example of the right-eye optical system 11R and the left-eye optical system 11L in the present embodiment will be described below. The right-eye optical system 11R and the left-eye optical system 22L are optical systems having same arrangement. Therefore, the description will be made by showing numerical example for one optical system.

Figure 4:
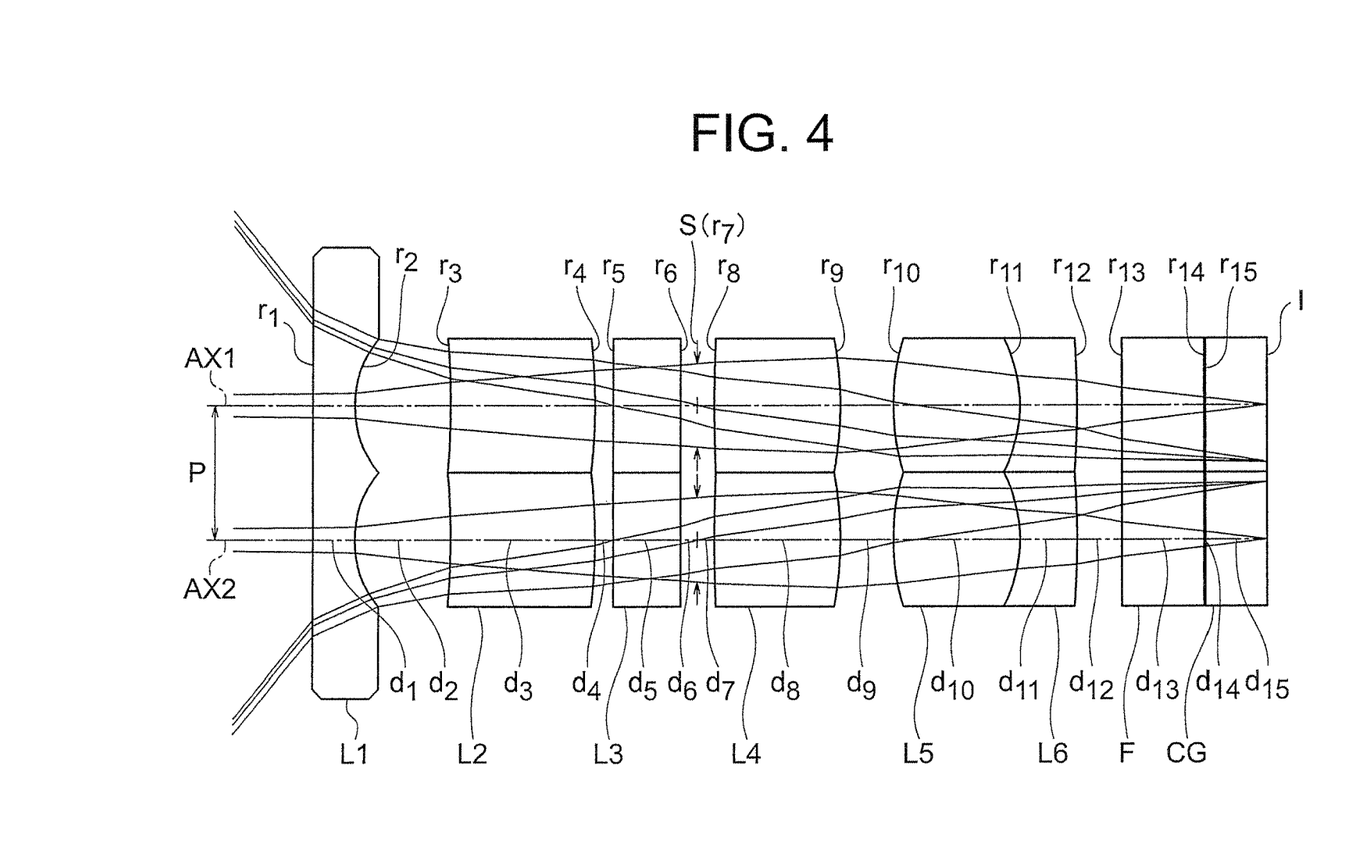
FIG. 4 is a diagram showing a cross-sectional arrangement of an optical system of the first embodiment.

Here, FIG. 4 is a diagram showing a cross-sectional arrangement of the right-eye optical system 11R and the left-eye optical system 11L.

The optical system includes in order from an object side, a planoconcave negative lens L1, a positive meniscus lens L2 having a convex surface directed toward an image side, a plane parallel plate L3, an aperture stop S, a biconvex positive lens L4, a biconvex positive lens L5, a negative meniscus lens L6 having a convex surface directed toward the image side, a filter F, and a cover glass CG. Here, the positive lens L5 and the negative lens L6 are cemented. Moreover, a space d14 between the filter F and the cover glass CG is an adhesive layer.

Furthermore, the plane parallel plate L3 is a an infra-red absorbing filter and a YAG (yttrium aluminum garnet) laser cut coating is applied to an object side thereof, and an LD laser cut coating is applied to an image side thereof.

A distance P between an optical axis AX1 and an optical axis AX2 is 1 mm corresponding to the parallax. In FIG. 4, axial light beams and off-axis light beams (angle of view 100 degrees and image height 0.429) are shown.

Numerical data of the example is shown below. Regarding symbols, r is a radius of curvature of each lens surface, d is a distance between two lens surfaces, nd is a refractive index for a d-line of each lens, and νd is Abbe's number for each lens.

Example 1 (refer to FIG. 4 for surface nos.)

| | Unit mm Surface data | | | |
|---|---|---|---|---|
| Surface no. | r | d | nd | νd |
| 1 | ∞ | 0.325 | 1.88815 | 40.76 |
| 2 | 0.7696 | 0.741 | | |
| 3 | −5.9424 | 1.112 | 1.85504 | 23.78 |
| 4 | −4.3921 | 0.1438 | | |
| 5 | ∞ | 0.52 | 1.49557 | 75 |
| 6 | ∞ | 0.13 | | |
| 7 (Stop) | ∞ | 0.1321 | | |
| 8 | 10.3317 | 0.9666 | 1.83932 | 37.16 |
| 9 | −2.4443 | 0.4076 | | |
| 10 | 1.7094 | 0.9669 | 1.69979 | 55.53 |
| 11 | −1.0787 | 0.4351 | 1.93429 | 18.9 |
| 12 | −7.3865 | 0.3426 | | |
| 13 | ∞ | 0.65 | 1.51825 | 64.14 |
| 14 | ∞ | 0.013 | 1.515 | 64 |
| 15 | ∞ | 0.455 | 1.507 | 63.26 |
| Image plane | ∞ | | | |

(Second Embodiment)

Next, an endoscope apparatus according to a second embodiment of the present invention will be described below. Same reference numerals are used for components same as in the first embodiment, and repetitive description is omitted.

Figure 5A:
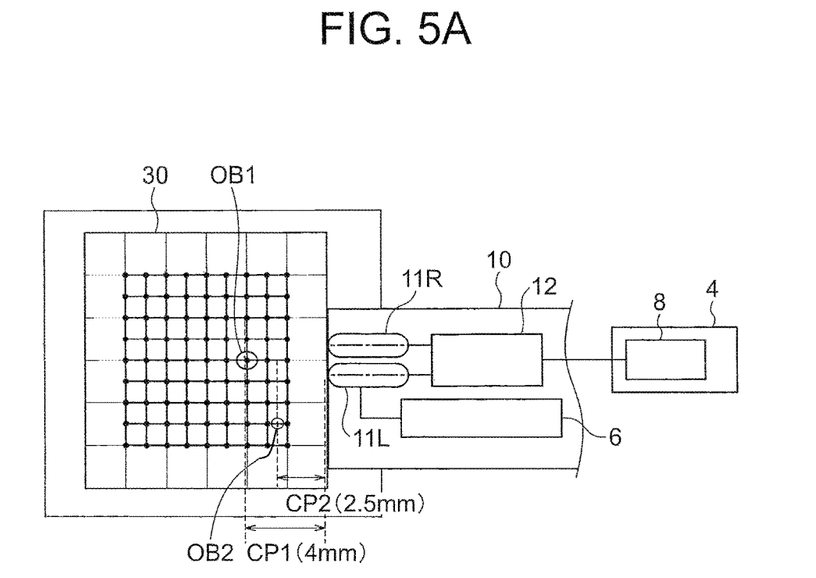
FIG. 5A is a diagram illustrating an object space of an endoscope apparatus according to a second embodiment.

FIG. 5A is a diagram showing a schematic arrangement of the endoscope apparatus of the present embodiment.

The endoscope apparatus includes a lens drive unit 6 which is a means which switches to at least two optical system focal points, and a CP value changing unit 8 which is a means which, when focused to an object at a far-point side, satisfies conditional expression (1), and when focus to an object at a near-point side, switches the value of CP to a value (CP2) smaller than a value of CP (CP1) when focused to an object at a far-point side.

Figure 5B:
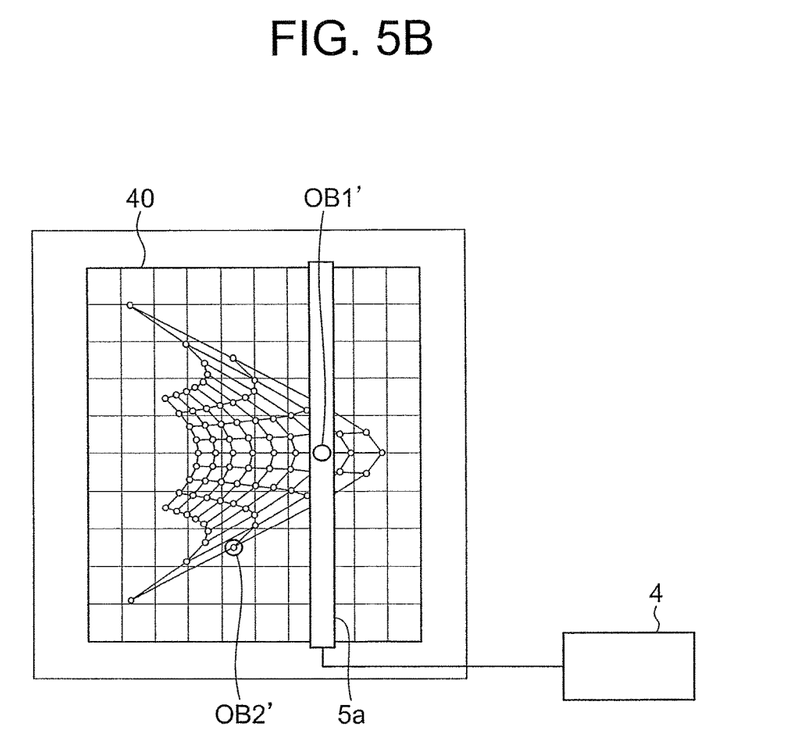
FIG. 5B is a diagram illustrating a reproducing space of the endoscope apparatus according to the second embodiment.

In the present embodiment, it is possible to switch to a far-point side focal point and a near-point side focal point by the lens drive unit 6. Moreover, in a case of the far-point side focal point, CP×(1+Dt1) is set to be 0.52. FIG. 5B is a diagram showing the reproducing space 40 in a state of the far-point side focal point. The object OB1 is observed as the object image OB1' on the monitor screen 5a. Moreover, the object OB2 (distance from a lens surface nearest to object is set to be 2.5 mm) which exists in a periphery of the object space is observed to be existing at the farther side than the monitor screen 5a as the object image OB2' in the reproducing space. Consequently, it is possible to make the angle of convergence θb in the reproducing space small. Accordingly, the observer can observe a stereoscopic image without fatigue.

Moreover, in the present embodiment, in a case of the near-point side focal point, lenses in the right-side optical system 11R and the left-side optical system 11L are driven by the lens drive unit 6. Accordingly, it is possible to switch from the far-point side focal point to the near-point side focal point. An arrangement is such that the distortion of the optical system does not fluctuate due to switching.

Figure 5C:
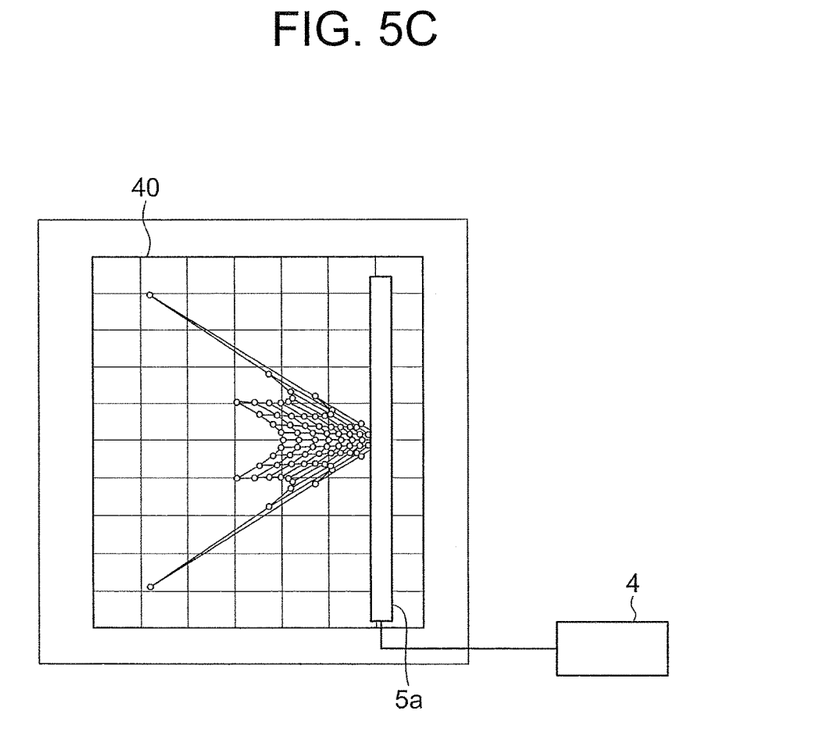
FIG. 5C is another diagram illustrating the reproducing space of the endoscope apparatus according to the second embodiment.

In the case of the near-point side focal point, the CP value is made to be 2.5 mm which is short, by the CP value changing unit. FIG. 5c is a diagram showing the reproducing space 40 in a state of the near-point side focal point. As it is evident from FIG. 5C, since an object in the overall area of the depth of field (2.5 mm to 5 mm) is reproduced in the depth direction from the monitor screen 5a, the observer can fuse images without fatigue.

Moreover, in the state of the near-point side focal point, CP×(1+Dt1) is 0.325 which is more than 0.3. Therefore, it is possible to fuse the overall depth area without fatigue. In the near-point side focal point, since an original depth width is narrow, the fusion of images is possible even in a case of not more than 0.3.

Numerical examples of the present invention are shown below.

Figure 6:
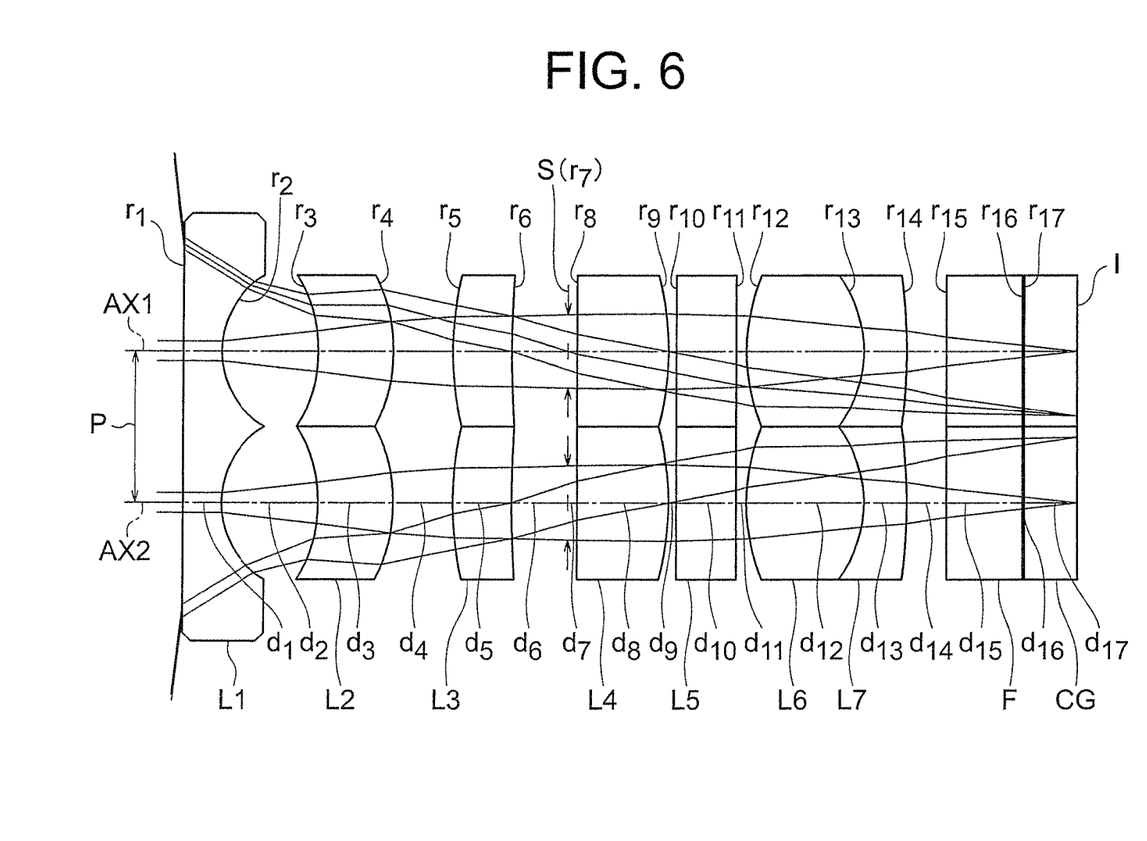
FIG. 6 is a diagram showing a cross-sectional arrangement of an optical system of the second embodiment.

Here, FIG. 6 is a diagram showing a cross-sectional arrangement of the right-eye optical system 11R and the left-eye optical system 11L.

The optical system includes in order from an object side, a planoconcave negative lens L1, a negative meniscus lens L2 having a convex surface directed toward an image side, a positive meniscus lens L3 having a convex surface directed toward the object side, an aperture stop S, a biconvex positive lens L4, a plane parallel plate L5, a biconvex positive lens L6, a negative meniscus lens L7 having a convex surface directed toward the image side, a filter F, and a cover glass CG. Here, the positive lens L6 and the negative lens L7 are cemented. Moreover, a space d16 between the filter F and the cover glass CG is an adhesive layer.

A distance P between an optical axis AX1 and an optical axis AX2 is 1 mm corresponding to parallax. In FIG. 6, axial light beams and off-axial light beams (angle of view 166 degrees and image height 0.429) are shown.

In a case of switching from the far-point side focal point to the near-point side focal point, the lens L3 moves along the optical axis toward the image pickup element 12 by the lens drive unit 6. Accordingly, it is possible to move the focal point to the near-point side.

<Far-Point Side Focal Point>

Depth of field 5 mm to 100 mm,

Angle of view 166 degrees

Parallax between the left-eye optical system and the right eye optical system 1 mm (inward angle θa at CP value 4 mm 14.3 degrees), Distortion in length at the maximum image height −0.87, CP value 4 mm, $$CP \times (1+Dt1) = 0.52$$

<Near-Point Side Focal Point>

Depth of field 2.5 mm to 5 mm,

Angle of view 166 degrees,

Parallax between left-eye optical system and right eye optical system 1 mm (inward angle at CP value 2.5 mm 22.6 degrees), Distortion in length at the maximum image height −0.87, CP value 2.5 mm, $$CP \times (1+Dt1) = 0.325$$

Example 2 (refer to FIG. 6 for surface nos.)

Unit mm
Surface data

| Surface no. | r | d | nd | vd |
|---|---|---|---|---|
| 1 | ∞ | 0.25 | 1.88815 | 40.76 |
| 2 | 0.592 | 0.6331 | | |
| 3 | −0.9641 | 0.49 | 1.85504 | 23.78 |
| 4 | −1.1345 | 0.3899 | | |
| 5 | 2.11 | 0.3917 | 1.58482 | 40.75 |
| 6 | 12.2107 | 0.3598 | | |
| 7 (Stop) | ∞ | 0.061 | | |
| 8 | 22.4495 | 0.5905 | 1.57124 | 56.36 |
| 9 | −1.9442 | 0.05 | | |
| 10 | ∞ | 0.4 | 1.49557 | 75 |
| 11 | ∞ | 0.0656 | | |
| 12 | 1.3335 | 0.7598 | 1.69979 | 55.53 |
| 13 | −0.8346 | 0.2798 | 1.93429 | 18.9 |
| 14 | −3.6567 | 0.252 | | |
| 15 | ∞ | 0.5 | 1.51825 | 64.14 |
| 16 | ∞ | 0.01 | 1.515 | 64 |
| 17 | ∞ | 0.35 | 1.507 | 63.26 |
| Image plane | ∞ | | | |

Numerical values of conditional expression (1) for the endoscope apparatuses according to the first embodiment and the second embodiment are shown below. As a visual range, the optimum visual range is used. The visual range is a critical distance that allows identifying each pixel forming a screen, when a person having eyesight of 1.0 views a resolution of 1920×1080. In an example 2, a case in which the focal point is adjusted to the far-end side will be described. Moreover, regarding Dt1, distortion values for optical systems of an example 1 and the example 2 will be described.

(Case in Which a Size of the Monitor 5 is 26 Inches)
Distance from which the observer views monitor is let to be 1 m, and
width of eyes of observer is let to be 65 mm.
In this case, the angle of convergence θb becomes 3.7 degrees.
Case in which object is in a depth of field on the near-point side
Parallax
Example 1: 1
Example 2: 1
Dt1
Example 1: −0.34
Example 2: −0.87
Object distance from surface nearest to object of optical system
Example 1: 7.0
Example 2: 5.0
Inward angle θa
Example 1: 8.2
Example 2: 11.4
Angle of convergence θb
Example 1: 3.7
Example 2: 3.0
Case of Reproducing Object on Monitor Screen
Object distance CP from surface nearest to object of optical system
Example 1: 7.0
Example 2: 4.0
Inward angle θa
Example 1: 8.2
Example 2: 14.3
Angle of convergence θb
Example 1: 3.7
Example 2: 3.7
CP×(1+Dt1)
Example 1: 4.6
Example 2: 0.5
(Case in Which the Size of the Monitor 5 is 32 Inches)
Distance from which the observer views monitor is let to be 1.3 m, and
width of eyes of observer is let to be 65 mm.
In this case, the angle of convergence θb becomes 2.9 degrees.
Case in which object is in the depth of field on the near-point side
Parallax
Example 1: 1
Example 2: 1
Dt1
Example 1: −0.34
Example 2: −0.87
Object distance from surface nearest to object of optical system
Example 1: 7.0
Example 2: 5.0
Inward angle θa
Example 1: 8.2
Example 2: 11.4
Angle of convergence θb
Example 1: 2.9
Example 2: 2.3
Case of Reproducing Object on Monitor Screen
Object distance CP from surface nearest to object of optical system
Example 1: 7.0
Example 2: 4.0
Inward angle θa
Example 1: 8.2
Example 2: 14.3
Angle of Convergence θb
Example 1: 2.9
Example 2: 2.9
CP×(1+Dt1)
Example 1: 4.6
Example 2: 0.5

Various embodiments of the present invention have been described above. However, the present invention is not limited to these embodiments, and embodiments in which arrangements in these embodiments are combined without departing from the scope of the invention are also in the category of the present invention.

For example, by having three or more optical systems, any two of the three or more optical systems may be selected, and pictorial images for the left eye and right eye may be created. Moreover, as a modification of the example 2, it may be applied to a variable magnification optical system in which the angle of view varies according to the fluctuation in the focal position.

As described above, the present invention is useful for an endoscope apparatus which is small-sized and which has a favorable optical performance.

An endoscope apparatus according to an embodiment of the present invention shows an effect that an easily viewable three-dimensional observation is possible in close observation.

What is claimed is:
1. An endoscope apparatus, comprising:
optical systems configured to form image pairs for a left-eye and a right-eye;
at least one image sensor configured to capture the image pairs and generate corresponding pictorial image pairs for the left eye and the right eye; and
an image processing apparatus which is configured to process a pictorial image pair from the image sensor and create a stereoscopic image pair that can be displayed on a monitor,
wherein the endoscope apparatus satisfies the following conditional expression (1):

$$0.3 < CP \times (1+Dt1) < 7, \text{ and } CP \leq 10 \qquad (1)$$

where:
CP denotes a distance (mm) to an object from a surface of the optical systems that is closest to the object, at which an amount of left and right shift of the left-eye pictorial image and the right-eye pictorial image is 0, at a center of the monitor, and
Dt1 denotes a distortion in length at a maximum image height.
2. The endoscope apparatus according to claim 1, comprising:
a lens driver configured to switch between at least two optical system focal points,
wherein the image processing apparatus, when focus is switched to an object at a far-point side, satisfies conditional expression (1), and when focus is switched to an object at a near-point side, switches a value of CP to a value that is smaller than a value of CP when focus is switched to an object at the far-point side, and
wherein the near-point side is closer to the optical systems than the far-point side.

3. The endoscope apparatus according to claim 1, wherein the number of the at least one image sensor is two, and "and the two image sensors capture one and the other images, respectively, of each image pair and each generates the corresponding pictorial image.

* * * * *